United States Patent [19]

Vecchietti et al.

[11] Patent Number: 4,999,359
[45] Date of Patent: Mar. 12, 1991

[54] HETEROCYCLIC ETHYLENE DIAMINE COMPOUNDS AND THEIR PHARMACEUTICAL COMPOSITIONS AND METHODS

[75] Inventors: Vittorio Vecchietti; Giuseppe Giardina, both of Milan, Italy

[73] Assignee: Dr. Lo Zambeletti S.p.A., Italy

[21] Appl. No.: 323,617

[22] Filed: Mar. 14, 1989

[30] Foreign Application Priority Data

Mar. 16, 1988 [GB] United Kingdom ............... 8806210
Oct. 7, 1988 [GB] United Kingdom ............... 8823562

[51] Int. Cl.$^5$ ............... A61K 31/435; C07D 471/04
[52] U.S. Cl. ............... 514/301; 514/215; 514/300; 514/302; 514/303; 514/367; 514/393; 514/403; 514/410; 540/578; 540/580; 540/593; 546/113; 546/114; 546/115; 546/120; 546/122; 546/198; 546/199; 548/153; 548/323; 548/369; 548/453
[58] Field of Search ............... 546/114, 113, 115, 120, 546/122, 198, 199; 514/301, 215, 300, 302, 303, 367, 393, 403, 410; 540/578, 580, 593; 548/153, 323, 369, 453

[56] References Cited

U.S. PATENT DOCUMENTS 4,806,547 2/1989 Giardina et al. ............... 546/146

FOREIGN PATENT DOCUMENTS 254545 1/1988 European Pat. Off. .
261842 3/1988 European Pat. Off. .

Primary Examiner—Mary C. Lee
Assistant Examiner—Bernard I. Dentz
Attorney, Agent, or Firm—Jacobs & Jacobs

[57] ABSTRACT

A compound, or a solvate or salt thereof, of formula I:

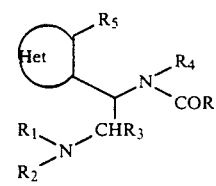

in which:
R.CO— is an acyl group containing a substituted or unsubstituted carbocyclic aromatic or heterocyclic aromatic group;
$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups or together form a $C_{2-8}$ branched or linear polymethylene or $C_{2-6}$ alkenylene group, optionally substituted with a hetero-atom;
$R_3$ is hydrogen, $C_{1-6}$ alkyl, or phenyl or $R_3$ together with $R_1$ form a —(CH$_2$)$_3$— or —(CH$_2$)$_4$— group;
$R_4$ is $C_{1-6}$ alkyl, or phenyl;
$R_5$ is hydrogen or together with $R_4$ forms a —(CH$_2$)$_n$— group in which n=1, 2 or 3; and 'Het' is an optionally substituted single or fused ring heterocyclic group, containing from 5 to 12 ring atoms and comprising up to four hetero-atoms in the or each ring selected from oxygen, nitrogen and sulphur, with the proviso that when, simultaneously, $R_1$ and $R_2$ together are linear butylene, $R_3$ is hydrogen, $R_4$ is methyl, $R_5$ is hydrogen and R is 3,4-dichlorophenyl, 'Het' is not pyridyl, is useful for the treatment of pain.

10 Claims, No Drawings

HETEROCYCLIC ETHYLENE DIAMINE COMPOUNDS AND THEIR PHARMACEUTICAL COMPOSITIONS AND METHODS

This invention is concerned with novel heterocyclic derivatives, processes for their preparation, and their use in medicine, particularly as analgesics.

Compounds which are kappa-receptor agonists act as analgesics through interaction with kappa opioid receptors. The advantage of these agonists over the classical $\mu$-receptor agonists, such as morphine, lies in their ability to cause analgesia while being devoid of morphine-like behavioural effects and addition liability.

EP-A-261842 (Zambeletti) discloses a group of N'-acylated-[1-(phenyl or benzyl)]-1,2-ethylene diamines which exhibit kappa-receptor agonism without the behavioural effects of morphine and morphine analogues, and which are thus of potential therapeutic utility as analgesics.

EP-A-254545 (ICI) discloses a group of diamine compounds which are said to possess analgesic activity. Some of these compounds have certain structural similarities to the compounds of EP-A-261842; in particular compound No. 51 of EP-A-254545 has a structure in which the phenyl nucleus of a compound within the scope of EP-A-261842 is replaced by a pyridyl group.

A novel class of heterocyclic derivatives which are structurally related to the compounds of the above two documents has now been discovered which exhibit potent kappa-receptor agonism without the aforementioned undesirable behavioural effects.

According to the present invention there is provided a compound, or a solvate or salt thereof, of formula I:

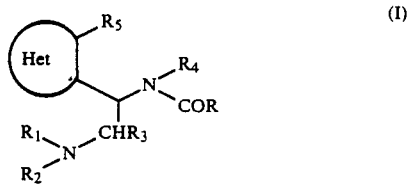

(I)

in which:

R.CO— is an acyl group containing a substituted or unsubstituted carbocyclic aromatic or heterocyclic aromatic group;

$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups or together form a $C_{2-8}$ branched or linear polymethylene or $C_{2-6}$ alkenylene group, optionally substituted with a hetero-atom;

$R_3$ is hydrogen, $C_{1-6}$ alkyl, preferably methyl or ethyl, or phenyl, or $R_3$ together with $R_1$ form a —$(CH_2)_3$— or —$(CH_2)_4$— group;

$R_4$ is $C_{1-6}$ alkyl, preferably methyl or ethyl, or phenyl;

$R_5$ is hydrogen or together with $R_4$ forms a —$(CH_2)_n$— group in which n=1, 2 or 3; and 'Het' is an optionally substituted single or fused ring heterocyclic group, preferably having aromatic character, containing from 5 to 12 ring atoms and comprising up to four hetero-atoms in the or each ring selected from oxygen, nitrogen and sulphur, with the proviso that when, simultaneously, $R_1$ and $R_2$ together are linear butylene, $R_3$ is hydrogen, $R_4$ is methyl, $R_5$ is hydrogen and R is 3,4-dichlorophenyl, 'Het' is not pyridyl.

When used herein, the term 'carbocyclic aromatic group' includes single or fused rings, having 6 to 12 ring carbon atoms, and the term 'heterocyclic aromatic group' includes single or fused rings having 5 to 12 ring atoms, comprising up to four hetero-atoms in the or each ring, selected from oxygen, nitrogen and sulphur.

When the carbocyclic or heterocyclic group is a fused two ring system, one or both single rings may be aromatic in character. Suitably, one of the rings is aromatic and the other is non-aromatic.

Preferably, 'Het' is a single ring containing one or two sulphur or nitrogen atoms.

When $R_1$ and $R_2$ are $C_{1-6}$ alkyl groups, examples are methyl, ethyl, propyl, butyl, pentyl or hexyl groups, preferably methyl.

Examples of $C_{2-6}$ alkenyl groups are 1- and 2- propenyl; an example of a $C_{3-6}$ cycloalkyl group is cyclopropyl, and an example of a $C_{4-12}$ cycloalkylalkyl group is cyclopropylmethyl.

When $R_1$ and $R_2$ together form a linear or branched polymethylene group, examples are propylene, butylene, pentylene or hexylene, preferably butylene or 1-methyl-butylene. As an alkenylene group, $R_1$-$R_2$ may be typically —$CH_2$—$CH=CH$—$CH_2$—. Examples of hetero-atoms are oxygen and sulphur, particularly oxygen, and a suitable hetero-atom substituted polymethylene group is —$CH_2CH_2OCH_2CH_2$—.

When 'Het' is an optionally substituted single ring heterocyclic group, examples are thienyl, furyl, pyrryl, imidazolyl, pyrazolyl, thiazolyl and pyridyl, preferably thienyl; and when 'Het' is a fused ring heterocyclic group, examples are benzofuranyl, benzothienyl, indolyl and quinolyl.

The group R preferably has the formula (II)

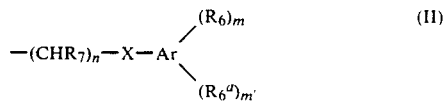

(II)

in which
n is 0, 1 or 2,
m is 0, 1 or 2,
m' is 0, 1 or 2, provided m+m'$\leq$2;
X is a direct bond, or O, S or $NR_8$ in which $R_8$ is hydrogen or $C_{1-6}$ alkyl;
Ar is a substituted or unsubstituted carbocyclic aromatic or heterocyclic aromatic group, each of $R_6$ and $R_6{}^a$ is $C_{1-6}$ alkyl, $C_{2-6}$ alkenyl, $C_{1-6}$ haloalkyl, $C_{2-6}$ haloalkenyl, $C_{2-6}$ haloalkynyl, aryl, aralkyl, hydroxy, $C_{1-6}$ alkoxy, $C_{1-6}$ haloalkoxy, thiol, $C_{1-6}$ alkylthio, $C_{1-6}$ haloalkylthio, halogen, nitro, cyano, carboxy, $C_{1-6}$ alkoxy-, aryloxy- or aralkoxycarbonyl, carbamoyl, sulfonyl, sulfamoyl, or when m is 2 and m' is O, two $R_6$'s form a $C_{3-6}$ polymethylene group, and $R_7$ is hydrogen or $C_{1-6}$ alkyl.

When $R_6$ or $R_6{}^a$ is aryl it may be phenyl, and when each is aralkyl it may be phenyl $C_{1-6}$ alkyl, such as benzyl.

Examples of $R_6$ or $R_6{}^a$ are —$CF_3$, —Cl, Br, —$OCF_3$, —$OCHF_2$, —$OCF_2CF_2H$, —$OCCl_2CF_3$. When two $R_6$'s are linked they may form a fused cyclopentyl or cyclohexyl ring.

Examples of $R_7$ are methyl and ethyl, and preferably $R_7$ is hydrogen.

Preferably Ar is phenyl and $R_6$ or $R_6{}^a$ is preferably in the meta- and/or para-position.

Preferably, $R_6$ or $R_6{}^a$ is bromine, chlorine, or —$CF_3$, particularly in the meta- and/or para-position.

X is typically oxygen or a direct bond, and n is typically 0 or 1.

Examples of R are:

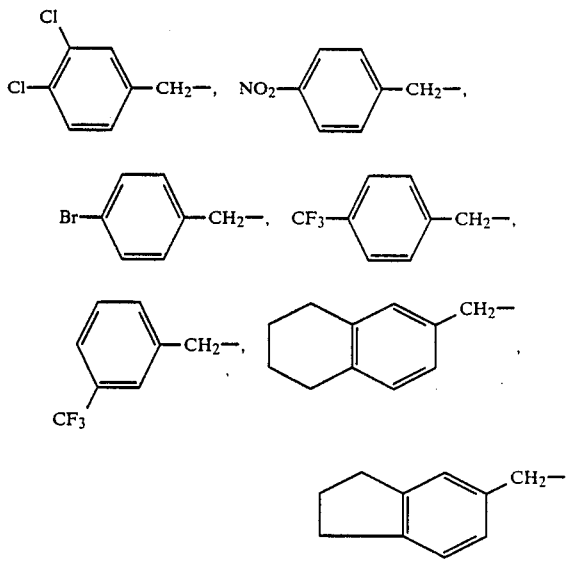

Examples of compounds of the invention are:
N-methyl-N-[1-(thien-3-yl)-2-(pyrrolidin-1-yl) ethyl-3,4-dichlorobenzene acetamide;
4-(pyrrolidin-1-yl)methyl-5-(3,4-dichlorophenyl)acetyl-4,5,6,7-tetrahydrothieno[3,2-c]pyridine
4-(pyrrolidin-1-yl)methyl-5-(4-trifluoromethylphenyl) acetyl-4,5,6,7-tetrahydrothieno [3,2-c] pyridine;
4-(piperidin-1-yl)methyl-5-(3,4-dichlorophenyl)acetyl-4,5,6,7-tetrahydrothieno [3,2-c] pyridine;
4-dimethylaminomethyl-5-(3,4-dichlorophenyl)acetyl-4,5,6,7-tetrahydrothieno [3,2-c] pyridine;
4-dimethylaminomethyl-5-(4-fluoromethylphenyl)acetyl-4,5,6,7-tetrahydrothieno [3,2-c] pyridine;
(+)-4-(pyrrolidin-1-yl)methyl-5-(3,4-dichlorophenyl) acetyl-4,5,6,7-tetrahydrothieno [3,2-c] pyridine;
(−)-4-(pyrrolidin-1-yl)methyl-5-(3,4-dichlorophenyl) acetyl-4,5,6,7-tetrahydrothieno [3,2-c] pyridine;
(−)-4-(piperidin-1-yl)methyl-5-(3,4-dichlorophenyl) acetyl-4,5,6,7-tetrahydrothieno [3,2-c] pyridine;
(+)-4-(piperidin-1-yl)methyl-5-(3,4-dichlorophenyl) acetyl-4,5,6,7-tetrahydrothieno [3,2-c] pyridine;
4-(piperidin-1-yl)methyl-5-(4-trifluoromethylphenyl) acetyl-4,5,6,7-tetrahydrothieno [3,2-c] pyridine;
(−)-4-(piperidin-1-yl)methyl-5-(4-trifluoromethylphenyl)acetyl-4,5,6,7-tetrahydrothieno [3,2-c] pyridine;
(+)-4-(piperidin-1-yl)methyl-5-(4-trifluoromethylphenyl)acetyl-4,5,6,7-tetrahydrothieno [3,2-c] pyridine;
1-(pyrrolidin-1-yl)methyl-2-(3,4-dichlorophenyl) acetyl-1,2,3,4-tetrahydro-5H-pyrido [4,3-b] indole;
1-(piperidin-1-yl)methyl-2-(3,4-dichlorophenyl) acetyl-1,2,3,4-tetrahydro-5H-pyrido [4,3-b] indole;
4-[1-(1-dimethylamino)ethyl]-5-(3,4-dichlorophenyl) acetyl-4,5,6,7-tetrahydrothieno [3,2-c] pyridine;
4-[1-(dimethylamino)ethyl]-5-(3,4-dichlorophenyl) acetyl-4,5,6,7-tetrahydrothieno [3,2-c] pyridine;
4-(piperidin-1-yl)methyl-5-(5,6,7,8-tetrahydronaphth-2-yl)acetyl-4,5,6,7-tetrahydrothieno [3,2-c] pyridine;
4-(piperidin-1-yl)methyl-5-(indan-5-yl)acetyl-4,5,6,7-tetrahydrothieno [3,2-c] pyridine;
4-(pyrrolidin-1-yl)methyl-5-(5,6,7,8-tetrahydronaphth-2-yl)acetyl-4,5,6,7-tetrahydrothieno [3,2-c] pyridine;
4-(pyrrolidin-1-yl)methyl-5-(indan-5-yl)acetyl-4,5,6,7-tetrahydrothieno [3,2-c] pyridine;
4-(pyrrolidin-1-yl)methyl-5-(3,4-dichlorophenyl)acetyl-4,5,6,7-tetrahydroimidazo [4,5-c] pyridine;
(+)-4-(pyrrolidin-1-yl)methyl-5-(5,6,7,8-tetrahydronaphth-2-yl)acetyl-4,5,6,7-tetrahydrothieno [3,2-c] pyridine;
(−)-4-(pyrrolidin-1-yl)methyl-5-(5,6,7,8-tetrahydronaphth-2-yl)acetyl-4,5,6,7-tetrahydrothieno [3,2-c] pyridine; or a salt and/or solvate thereof.

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates.

The present invention also provides a process for the preparation of a compound of formula I which comprises reacting a compound of formula (III)

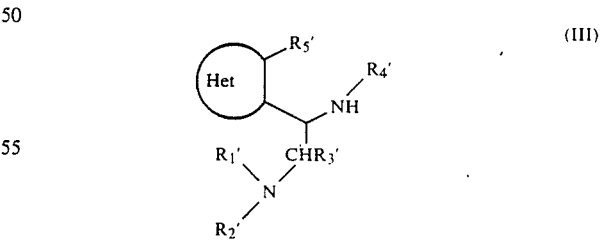

in which $R_1'$ to $R_5'$ are $R_1$ to $R_5$ as defined for formula (I) or a group or atom convertible to $R_1$ to $R_5$ and Het is as defined for formula (I), with a compound of formula

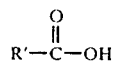

or an active derivative thereof, in which R' is R as defined for formula (I) or a group convertible to R, to form a compound of formula (Ia)

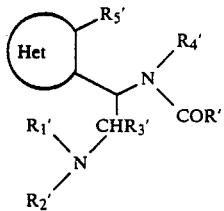 (Ia)

and optionally thereafter performing one or more of the following steps:
(a) where R' and R₁' to R₅' are other than R, and R₁ to R₅, converting any one of R' and R₁' to R₅' to R₁ to R₅ to obtain a compound of formula (I),
(b) where R' and R₁' to R₅' are R and R₁ to R₅, converting any one of R and R₁ to R₅ to another R and R₁ to R₅ to obtain a compound of formula (I),
(c) forming a salt and/or solvate of the obtained compound of formula (I).

Suitable active derivatives of

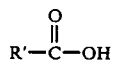

are acid chlorides or acid anhydrides. Another suitable derivative is a mixed anhydride formed between the acid and an alkyl chloroformate.

For example, in standard methods well known to those skilled in the art, the compound of formula (III) may be coupled:
(a) with an acid chloride in the presence of an inorganic or organic base,
(b) with the acid in the presence of dicyclohexyl carbodiimide, N-dimethylaminopropyl-N'-ethyl carbodiimide or carbonyl diimidazole,
(c) with a mixed anhydride generated in situ from the acid and an alkyl (for example ethyl)chloroformate.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention.

For example, R₁' and R₂' may be alkyl groups and converted to R₁'/R₂' hydrogen atoms by conventional amine dealkylation. When R₁' or R₂' is benzyl or substituted benzyl it may be converted to an R₁ or R₂ hydrogen atom by catalytic hydrogenation or other method of reduction. R₁' and R₂' as hydrogen atoms may be converted to R₁ and R₂ alkyl groups by conventional amine alkylation, or by acylation followed by reduction. R₁' and R₂' are preferably R₁ and R₂ respectively.

The above described process will generally provide a diastereoisomeric mixture which can subsequently separated into isomers by column chromatography.

The compound

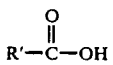

is typically of the formula (IIa)

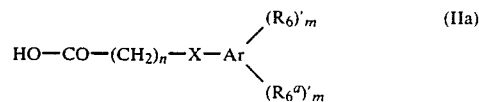

in which R₆' is R₆ and (R₆ᵃ)' is R₆ᵃ are as defined for formula (II), or a group or atom convertible to R₆ or R₆ᵃ, the other variables being as defined for formula (II).

Conversions of substituents R₆' or (R₆ᵃ)' on the aromatic group Ar to obtain R₆ or R₆ᵃ are generally known in the art of aromatic chemistry. R₆' is preferably R₆ and (R₆ᵃ)' is preferably R₆ᵃ.

The compounds of formula I may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

As mentioned before, the compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

Compounds of formula (III) in which R₅' is hydrogen may be prepared by reductive amination of a compound of formula (IV)

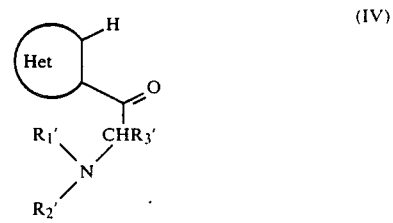

in which R₁', R₂', R₃' and Het are as defined for formula (III), with an amine of formula R'₄NH₂, preferably in the presence of a mixed hydride such as NaCNBH₃ or NaBH₄.

Compounds of formula (IV) are known compounds (J.A.C.S. 74 (1952), 3676; Ber. 84 (1951), 147; J.A.C.S. 66 (1944), (1327) or can be prepared from known compounds by known methods.

Compounds of formula (III) in which R₃' is hydrogen and R'₄ and R'₅ together form a —(CH₂)ₙ— group (compounds of formula IIIb) may conveniently be prepared according to the following reaction scheme:

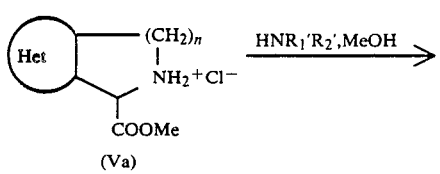

(Va)

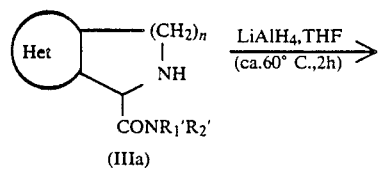

(IIIa)

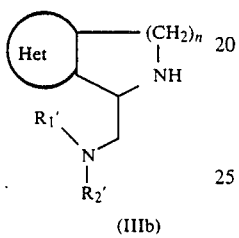

(IIIb)

In this reaction scheme, compounds of formula (IIIa) are prepared from compounds of formula (Va) by reaction with secondary amines (HNR$_1$'R$_2$') in a suitable solvent such as methanol, preferably at a temperature of from 0° to 90° C. The compounds of formula (IIIa) are then converted to compounds of formula (IIIb) by reduction with a mixed hydride such as LiAlH$_4$, or (BH$_3$)$_2$, preferably in an inert medium such as THF. A temperature of about 60° C. and a reaction time of about 2 hours has been found to produce advantageous results.

Compounds of formula (Va) are prepared by known methods from known compounds (Heterocycles 16 (n.1) (1981), 35; DE-Al No. 3529960.

Alternatively, compounds of formula (III) in which R$_4$' and R$_5$' together form a —(CH$_2$)n— group (compounds of formula IIIc) may conveniently be prepared according to the following reaction scheme:

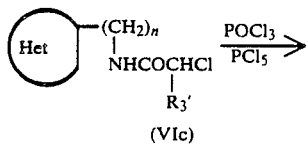

(VIc)

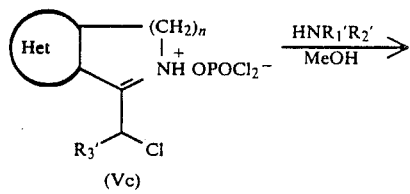

(Vc)

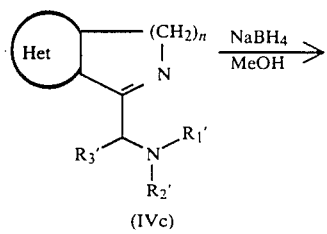

(IVc)

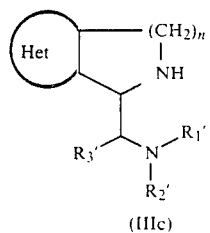

(IIIc)

In this reaction scheme, compounds of formula (IIIc) are prepared by treating compounds of formula (VIc) with phosphorous oxychloride and phosphorous pentachloride at room temperature followed by filtration of the hygroscopic material.

The compounds of formula (Vc) are then converted to compounds of formula (IVc) by reaction with secondary amines (HNR$_1$'R$_2$') in a suitable solvent such as methanol, preferably at a temperature of from 0° to 90° C.

The compounds of formula (IVc) are then treated with a mixed hydride, such as NaBH$_4$ or NaCNBH$_3$, preferably in a protic solvent such as methanol, to obtain compounds of formula (IIIc).

A temperature of from 0° to 25° C. and a reaction time of about 2 hours have been found to produce advantageous results.

The compounds of formula (VIc) are known compounds, or can be prepared from known compounds by known methods (see for example Synthetic Communications, 5(2), 79–86 (1975).

The compounds of formula (III) are novel and form a further aspect of the present invention.

The activity of the compounds of formula (I) in standard analgesic tests indicates that they are of therapeutic utility in the treatment of pain.

Accordingly the present invention also provides a compound of formula (I), or a pharmaceutically acceptable salt or solvate thereof, for use as an active therapeutic substance, particularly for use in treating pain.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method of treating pain in mammals, particularly in humans, which comprises administering an effective amount of a compound of formula (I), or pharmaceutically acceptable salt or solvate thereof, to a sufferer.

Compounds of this invention and their preparation are illustrated in the following Examples, apart from Example 1 which is included for comparison purposes. The Descriptions illustrate the preparation of intermediate compounds.

Description 1

N-methyl-1-(3-pyridinyl)-2-(1-pyrrolidinyl)ethanamine 9 g (34.22 mmoles) of 1-(3-pyridinyl)-2-(1-pyrrolidinyl) ethanone dihydrochloride were suspended in 110 ml of tetrahydrofuran containing 20% of monomethylamine. After 15 mins. of stirring, 3.6 g (57.32 mmoles) of sodium cyanoborohydride were added at room temperature. After 24 h the reaction mixture was evaporated in vacuo to dryness. The residue was taken up with conc. NaOH solution and exhaustively extracted with diethyl ether. The organic solution was dried and evaporated in vacuo to dryness. 4.2 g of the crude product were obtained and used, without further purification, in the following step.

Example 1

N-methyl-N-[1-(pyridin-3-yl)-2-(pyrrolidin-1-yl)]ethyl-3,4-dichlorobenzene acetamide dimaleate 1.4 g (6.82 mmoles) of N-methyl-1-(3-pyridinyl)-2-(1-pyrrolidinyl) ethanamine were dissolved in 20 ml of dry chloroform and the solution cooled at 0° C.

1.7 g (7.50 mmoles) of 3,4-dichlorophenylacetylchloride dissolved in 10 ml of dry chloroform, were added dropwise to the solution.

The reaction mixture was allowed to reach room temperature, stirred 24 hours and evaporated in vacuo to dryness. The residue was treated with 1N NaOH and extracted with ethyl acetate. The organic solution was dried, evaporated in vacuo to dryness and the residual oil was chromatographed on silica gel, eluting with $CH_2Cl_2$ containing increasing amounts of MeOH (0.5-2.5%), to afford 1.6 g of the free base. Acetone was added and the obtained solution brought to acidic pH with an acetone solution of maleic acid. The precipitate was filtered, washed and dried, to yield 1.4 g of the title compound.

$C_{20}H_{23}Cl_2N_3O.2C_4H_4O_4$.

M.P. = 130°-132° C. M.W. = 624.466.

N.M.R. ($CDCl_3$): δ9.8 (s) 4H; 8.6 (m) 2H; 7.0-7.8 (m) 5H; 80 Mhz 6.4 (m) 1H; 6.25 (s) 4H; 3.4-4.4 (m) 8H; 2.8 (s) 3H; 2.0-2.2 (m) 4H.

Description 2

N-methyl-1(thien-3-yl)-2-(pyrrolidin-1-yl)ethanamine 7.5 g (32.4 mmoles) of 1-(3-thienyl)-2-(1-pyrrolidinyl) ethanone hydrochloride were suspended in 90 ml of tetrahydrofuran containing 20% of monomethylamine.

After 15 mins. of stirring, 2.2 g (35.04 mmoles) of sodium cyanoborohydride were added at room temperature.

After 24 h the reaction mixture was evaporated in vacuo to dryness; the residue was taken up with 10N NaOH solution and exhaustively extracted with diethyl ether.

The organic solution was dried and evaporated to dryness. 4.9 g of the crude product were obtained and used, without further purification, for the following step.

Example 2

N-methyl-N-[1-(thien-3-yl)-2-(pyrrolidin-1-yl)]ethyl-3,4-dichlorobenzene acetamide hydrochloride 1 g (4.76 mmoles) of N-methyl-1-(3-thienyl)-2-(1-pyrrolidinyl) ethanamine was dissolved in 50 ml of dry chloroform and the solution cooled at 0° C.

1.2 g (5.30 mmoles) of 3,4-dichlorophenylacetylchloride, dissolved in 10 ml of dry chloroform, were added dropwise to the solution. The reaction mixture was allowed to reach room temperature, stirred 24 hours and evaporated in vacuo to dryness.

The residue was treated with 1N NaOH and extracted with ethyl acetate. The organic layer was dried, evaporated to dryness and the residual oil was chromatographed on silica gel, eluting with $CH_2Cl_2$ containing increasing amounts of MeOH (0.2-0.8%) to afford 1.4 g of the free base. Acetone was added and the obtained solution brought to acidic pH with HCl/diethyl ether.

1.2 g of the hydrochloride salt was collected and recrystallized from abs. ethanol, to yield 0.9 g of the title compound.

$C_{19}H_{22}Cl_2N_2OS.HCl$

M.P. = 214°-215° C. M.W. = 433.825.

Elemental analysis: Calcd. C, 52.59; H, 5.34; N, 6.45. Found C, 52.28; H, 5.29; N, 6.31. I.R. (KBr): 1640 cm$^{-1}$ (s) N.M.R. ($CDCl_3$): δ11.5 (s) 1H; 7.10-7.50 (m) 5H; 80 Mhz 6.95 (m) 1H; 6.85 (dd) 1H; 3.90 AB system 2H; 3.10-4.20 (m) 4H; 2.95 (s) 3H; 2.50-3.10 (m) 2H; 1.90-2.50 (m) 4H.

Description 3

4-(pyrrolidin-1-yl)carbonyl-4,5,6,7-tetrahydrothieno[3,2-c]pyridine 3.7 g (15.85 mmoles) of 4,5,6,7-tetrahydrothieno 3,2-C pyridine-4-carboxylic acid methylester hydrochloride were mixed with 13 ml of pyrrolidine and stirred 48 h at room temperature. The excess of pyrrolidine was evaporated in vacuo; the residue was treated with acq. $NH_3$, extracted with ethyl acetate and the organic solution was dried and evaporated in vacuo. The residual oil was chromatographed on silica gel, eluting with $CH_2Cl_2$ containing 0.5% of MeOH, to yield 2.2 g of the title compound.

N.M.R. ($CDCl_3$): δ7.05 (d) 1H; 6.65 (d) 1H; 4.80 (s) 1H; 80 Mhz 3.30-3.80 (m) 5H; 2.70-3.25 (m) 3H; 2.30 (s) 1H; 1.80-2.10 (m) 4H.

Description 4

4-(pyrrolidin-1-yl)methyl-4,5,6,7-tetrahydrothieno[3,2-c]pyridine 800 mg (21.0 mmoles) of lithium aluminium hydride were suspended in 25 ml of dry tetrahydrofuran under $N_2$ atmosphere.

2.2 g (9.32 mmoles) of 4-(1-pyrrolidinylcarbonyl)-4,5,6,7-tetrahydrothieno 3,2-C pyridine, dissolved in 30 ml of dry THF, were added dropwise and the reaction mixture heated 3 h at 60° C.

After an alkaline work-up, 2.1 g of the crude product were obtained and used, without further purification, for the following step.

Example 3

4-(pyrrolidin-1-yl)methyl-5-(3,4-dichlorophenyl)acetyl-4,5,6,7-tetrahydrothieno[3,2-c]pyridine hydrochloride monohydrate 2.1 g (9.46 mmoles) of 4-(1-pyrrolidinylmethyl)-4,5,6,7-tetrahydrothieno 3,2-C pyridine and 2.3 g (11.22 mmoles) of 3,4-dichlorophenylacetic acid were dissolved in 50 ml of dry methylene chloride.

4 g (19.42 mmoles) of dicyclohexylcarbodiimide dissolved in 25 ml of methylene chloride, were added dropwise to this solution, at −5° C.

The reaction mixture was allowed to reach room temperature, stirred 6 hours and left overnight.

The precipitated dicyclohexylurea was filtered off and the solution evaporated in vacuo to dryness.

The residual oil was chromatographed on silica gel, eluting with $CH_2Cl_2$, containing increasing amounts of MeOH (0.2-0.8%), to afford 3.5 g of the free base, which was dissolved in ethyl acetate and, the solution brought to acidic pH with HCl/diethyl ether.

The precipitate was filtered, washed and dried, to yield 3.0 g of the title compound.

$C_{20}H_{22}Cl_2N_2OS.HCl·H_2O$

M.P. = 153°-155° C. M.W. = 463.853

Elemental analysis: Calcd. C, 51.78; H, 5.43; N, 6.04; Cl, 22.93; S, 6.91; Found C, 51.67; H, 5.30; N, 6.01; Cl, 22.41; S, 6.92. I.R. (KBr): 1655 cm$^{-1}$ (s); 1635 cm$^{-1}$ (s) N.M.R. ($CDCl_3$): δ11.7 (s) 1H; 7.10-7.45 (m) 4H; 80 Mhz 6.80 (d) 1H; 6.10 (dd) 1H; 3.90 AB system 2H; 3.35-4.40 (m) 5H; 2.50-3.30 (m) 5H; 2.05-2.40 (m) 4H; 2.05 (s) $H_2O$.

Example 4

4-(pyrrolidin-1-yl)methyl-5-(4-trifluoromethylphenyl)acetyl-4,5,6,7-tetrahydrothieno[3,2-c]pyridine hydrochloride.

Prepared as ex. No. 3, from 1.4 g (7.29 mmoles) of 4-(pyrrolidin-1-yl)methyl-4,5,6,7-tetrahydrothieno[3,2-c]pyridine, 1.6 g (7.84 mmoles) of 4-trifluoromethylphenylacetic acetic acid and 2.6 g (12.62 mmoles) of dicyclohexylcarbodiimide in 50 ml of dry chloroform.

The silica gel chromatographic column was eluted with hexane, containing increasing amounts of ethyl acetate (5–50%), to afford 1.4 g of the free base, which was dissolved in 40 ml of ethyl acetate and the solution brought to acidic pH with HCl/diethyl ether.

The precipitate was filtered, washed and dried, to yield 1.0 g of the title compound.

$C_{21}H_{23}F_3N_2OS.HCl$
M.P.=221°–222° C.
M.W.=444.941.

Elemental analysis: Calcd. C,56.68; H,5.44; N,6.30; Cl,7.97; F,12.81; S,7.21; Found C,56.66; H,5.30; N,6.26; Cl,7.97; F,12.80; S,7.16. I.R. (KBr): 1630 (s); 1615 (m); 1335 (m) cm$^{-1}$ N.M.R. (CDCl$_3$): δ11.90 (broad, 1H); 7.35–7.65 (d, 4H); 80 Mhz. 7.25 (d, 1H); 6.75 (d, 1H); 6.10 (dd, 1H); 3.40–4.50 (m, 7H); 2.50–3.20 (m, 5H); 2.00–2.40 (m, 4H).

Description 3a

4-(piperidin-1-yl)carbonyl-4,5,6,7-tetrahydrothieno[3,2-c]pyridine

Prepared as Description No. 3, from 3 g (12.85 mmoles) of 4,5,6,7-tetrahydrothieno[3,2-c]pyridine-4-carboxylic acid methyl ester hydrochloride, and 20 ml (200 mmoles) of piperidine heated six days at 80° C.

The silica gel chromatographic column was eluted with CH$_2$Cl$_2$, containing increasing amounts of MeOH (0.2–0.4%), to yield 1.8 g of the title compound.

I.R. (KBr): 1640 (s) cm$^{-1}$

Description 4a

4-(piperidin-1-yl)methyl-4,5,6,7-tetrahydrothieno[3,2-c]pyridine

Prepared as Description No. 4, from 1.7 g (6.8 mmoles) of 4-(piperidin-1-yl)carbonyl-4,5,6,7-tetrahydrothieno[3,2-c]pyridine and 600 mg (15.79 mmoles) of lithium aluminium hydride in 50 ml of dry THF.

After an alkaline work-up, 1.6 g of the crude product were obtained and used, without further purification, for the following step.

N.M.R. (CDCl$_3$): δ6.9 (AB system, J=6.0 Hz, 2H); 2.2–4.1 80 Mhz (m, 12H); 1.4–1.8 (m, 6H).

Example 5

4-(piperidin-1-yl)methyl-5-(3,4-dichlorophenyl)acetyl-4,5,6,7-tetrahydrothieno[3,2-c]pyridine hydrochloride.

Prepared as ex. No. 3, from 400 mg (1.69 mmoles) of 4-(piperidin-1-yl)methyl-4,5,6,7-tetrahydrothieno[3,2-c]pyridine, 450 mg (2.20 mmoles) of 3,4-dichlorophenylacetic acid and 800 mg (3.88 mmoles) of dicyclohexylcarbodiimide in 30 ml of dry chloroform.

The silica gel chromatographic column was eluted with hexane, containing increasing amounts of ethyl acetate (5–40%), to afford 300 mg of the free base, which was dissolved in 20 ml of acetone and the solution brought to acidic pH with HCl/diethyl ether.

The precipitate was filtered, washed and dried, to yield 170 mg of the title compound.

$C_{21}H_{24}Cl_2N_2OS.HCl$
M.P.=213°–214° C.
M.W.=459.863.

Elemental analysis: Calcd. C,54.84; H,5.48; N,6.09; Cl,23.13; S,6.97; Found C,55.10; H,5.48; N,5.99; Cl,22.95; S,7.04. I.R. (KBr): 1655, 1645 (s); 1475, 1435, 1415 (m) cm$^{-}$N.M.R. (CDCl$_3$): δ11.4 (broad, 1H); 7.15–7.50 (m, 4H); 80 Mhz. 6.75 (d, 1H); 6.10 (dd, 1H); 3.25–4.65 (m, 7H); 2.45–3.05 (m, 5H); 1.75–2.05 (m, 6H).

Description 3b

4,5,6,7-tetrahydrothieno[3,2-c]pyridine-4-carboxamide-N,N-dimethyl

Prepared as Description No. 3, from 5 g (21.42 mmoles) of 4,5,6,7-tetrahydrothieno[3,2-c]pyridine-4-carboxylic acid methyl ester hydrochloride and 50 ml of a 33% dimethylamine-ethanolic solution heated two weeks at 80° C. in a Parr bomb apparatus.

The silica gel chromatographic column was eluted with CH$_2$Cl$_2$, containing increasing amounts of MeOH (0.1–0.3%), to yield 2.3 g of the title compound.

I.R. (KBr): 1640 (s) cm$^{-1}$

Description 4b

4-dimethylaminomethyl-4,5,6,7-tetrahydrothieno[3,2-c]pyridine

Prepared as Description No. 4, from 2.2 g (10.47 mmoles) of 4,5,6,7-tetrahydrothieno[3,2-c]pyridine-4-carboxamide-N,N-dimethyl and 800 mg (21.05 mmoles) of lithium aluminium hydride in 55 ml of dry THF.

After an alkaline work-up, 1.9 g of the crude product were obtained and used, without further purification, for the following step.

Example 6

4-dimethylaminomethyl-5-(3,4-dichlorophenyl)acetyl-4,5,6,7-tetrahydrothieno[3,2-c]pyridine hydrochloride.

Prepared as ex. No. 3, from 0.8 g (4.08 mmoles) of 4-dimethylaminomethyl-4,5,6,7-tetrahydrothieno[3,2-c]pyridine, 1.0 g (4.88 mmoles) of 3,4-dichlorophenylacetic acid and 1.7 g (8.25 mmoles) of dicyclohexylcarbodiimide in 40 ml of dry chloroform.

The silica gel chromatographic column was eluted with CH2Cl2, containing increasing amounts of MeOH (0.2–1%), to afford 1.4 g of the free base, which was dissolved in 50 ml of ethyl acetate and the solution brought to acidic pH with HCl/diethyl ether.

The precipitate was filtered, washed and dried, to yield 1.2 g of the title compound.

$C_{18}H_{20}Cl_2N_2OS.HCl$
M.P.=255°–256° C.
M.W.=419.801.

Elemental analysis: Calcd. C,51.50; H,5.04; N,6.67; Cl,25.34; S,7.64; Found C,51.48; H,4.96; N,6.60; Cl,25.12; S,7.80. I.R. (KBr): 1625 (s); 1470 (m); 1425 (m) cm$^{-1}$. N.M.R. (CDCl3+DMSO): δ10.40 (broad, 1H); 7.05–7.45 (m, 4H); 80 Mhz. 6.85 (d, 1H); 5.90 (dd, 1H); 2.50–4.30 (m, 14H).

Example 7

4-dimethylaminomethyl-5-(4-trifluoromethylphenyl)acetyl-4,5,6,7-tetrahydrothieno[3,2-c]pyridine 1.5 hydrochloride ¼ hydrate.

Prepared as ex. No. 3, from 1.0 g (5.10 mmoles) of 4-dimethylaminomethyl-4,5,6,7-tetrahydrothieno[3,2-c]pyridine, 1.3 g (6.37 mmoles) of 4-trifluoromethylphenylacetic acid and 2.10 g (10.19 mmoles) of dicyclohexylcarbodiimide in 50 ml of dry chloroform.

The silica gel chromatographic column was eluted with CH2Cl2, containing increasing amounts of MeOH (0.2–0.8%), to afford 1.5 g of the free base, which was dissolved in 40 ml of ethyl acetate and the solution brought to acidic pH with HCl/diethyl ether.

The precipitate was filtered, washed and dried, to yield 1.3 g of the title compound.

$C_{19}H_{21}F_3N_2OS.1.5HCl.¼H_2O$
M.P. = 257°–258° C.
M.W. = 443.143.

Elemental analysis: Calcd. C,51.49; H,5.27; N,6.32; Cl,11.99 F,12.86; S,7.24; Found C,50.99; H,5.13; N,6.19; Cl,11.62; F,13.25; S,7.30. I.R. (KBr): 1645 (s); 1435 (m); 1320 (s) cm$^{-1}$. N.M.R. (CDCl3): δ11.65 (broad, 1H); 7.40–7.90 (m, 4H); 80 Mhz. 7.15 (d, 1H); 6.90 (d, 1H); 5.95 (dd, 1H): 2.60–4.70 (m, 14H).

Example 8

(+)-4-(pyrrolidin-1-yl)methyl-5-(3,4-dichlorophenyl)acetyl-4,5,6,7-tetrahydrothieno[3,2-c]pyridine L(+) tartrate hemihydrate 1.38 g (3.37 mmoles) of the compound of Ex. No. 3 were dissolved in 40 ml of abs. ethanol. 556 mg (3.71 mmoles) of L(+) tartaric adic, dissolved in 20 ml of ethanol, were added to the hot solution of the free base.

After a gentle warming the solution was filtered and evaporated in vacuo to dryness.

The residue was dissolved in 30 ml of hot acetone and the diastereoisomeric salt crystallized on standing. The salt was recrystallized from acetone, containing 10% of abs. ethanol, up to a constant rotatory power, to yield 475 mg of the title compound.

$C_{20}H_{22}Cl_2N_2OS.C_4H_6O_6.½H_2O$
M.P. = 181°–183° C.
M.W. = 568.468.
$[\alpha]_D^{20} = +60.34$ (C=1, MeOH), Elemental analysis: Calcd. C, 50.70; H, 5.14; N, 4.93; Found C, 50.90; H, 5.14; N, 4.90.

A sample of tartrate salt was transformed into the free base by dissolving in acq. NH3 solution, extracting with ethyl ether and evaporating the solvent in vacuo. The base gave an:

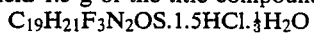

$[\alpha]_D^{20} = +82.68$ (C=1, CHCl3)

The NMR spectrum was identical to that obtained for the racemate.

Example 9

(−)-4-(pyrrolidin-1-yl)methyl-5-(3,4-dichlorophenyl)acetyl-4,5,6,7-tetrahydrothieno[3,2-c]pyridine D(−) tartrate hemihydrate The mother liquors of the first crystallization of example 8 were evaporated in vacuo to dryness. The residue was treated with acq. NH3 solution and extracted with ethyl ether to afford 700 mg (1.71 mmoles) of the enriched free base, which was dissolved in abs. ethanol. 280 mg (1.86 mmoles) of D(−) tartaric acid, dissolved in abs. ethanol, were added to the warm solution. After a gentle warming the solution was evaporated in vacuo to dryness.

The residue was dissolved in 50 ml of hot acetone and the diastereoisomeric salt crystallized on standing. The salt was recrystallized from acetone, containing 10% of abs. ethanol, up to a constant rotatory power, to yield 400 mg of the title compound.

$C_{20}H_{22}Cl_2N_2OS.C_4H_6O_6.½H_2O$
M.P. = 182°–183° C.
M.W. = 568.468.
$[\alpha]_D^{20} = -60.39$ (C=1, MeOH).

Elemental analysis: Calcd. C, 50.70; H, 5.14; N, 4.93; Found C, 50.72; H, 5.15; N, 4.83.

A sample of tartrate salt was transformed into the free base by dissolving in acq. NH3 solution, extracting with ethyl ether and evaporating the solvent in vacuo. The base gave an:

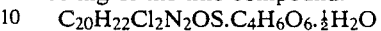

$[\alpha]_D^{20} = -80.98$ (C=1, CHCl3)

The NMR spectrum was identical to that obtained for the racemate.

Example 10

(−)-4-(piperidin-1-yl)methyl-5-(3,4-dichlorophenyl)acetyl-4,5,6,7-tetrahydrothieno[3,2-c]pyridine L(+) tartrate hemihydrate Prepared as Ex. No. 8, from 3.5 g (8.26 mmoles) of the compound of Ex. No. 5 and 1.30 g (8.66 mmoles) of L(+) tartaric acid in 60 ml of hot acetone.

After one day the distereoisomeric salt was filtered and recrystallized from acetone up to a constant rotatory power, to yield 1.3 g of the title compound.

$C_{21}H_{24}Cl_2N_2OS.C_4H_6O_6.½H_2O$
M.P. = 170°–171° C.
M.W. = 582.494.
$[\alpha]_D^{20} = -49.95$ (C=1, MeOH).

A sample of tartrate salt was transformed into the free base by dissolving in acq. NH3 solution, extracting with ethyl ether and evaporating the solvent in vacuo. The base gave an:

$[\alpha]_D^{20} = -85.58$ (C=1, CHCl3)

The NMR spectrum was identical to that obtained for the racemate.

Example 11

(+)-4-(piperidin-1-yl)methyl-5-(3,4-dichlorophenyl)acetyl-4,5,6,7-tetrahydrothieno[3,2-c]pyridine D(−) tartrate hemihydrate The mother liquors of the first crystallization of example 10 were evaporated in vacuo to dryness.

The residue was treated with acq. NH3 solution and extracted with ethyl ether to afford 2.0 g (4.72 mmoles) of the enriched free base, which was dissolved in 80 ml of hot acetone.

750 mg (4.99 mmoles) of D(−) tartaric acid were added and the diastereoisomeric salt crystallized on standing. The salt was recrystallized from acetone, up to a constant rotatory power, to yield 1.5 g of the title compound.

$C_{21}H_{24}Cl_2N_2OS.C_4H_6O_6.½H_2O$
M.P. = 171°–172° C.
M.W. = 582.494.

$[\alpha]_D^{20} = +49.46$ (C=1, MeOH).

Elemental analysis: Calcd. C, 51.54; H, 5.36; N, 4.80; Found C, 51.77; H, 5.36; N, 4.79.

A sample of tartrate salt was transformed into the free base by dissolving in acq. NH3 solution, extracting with ethyl ether and evaporating the solvent in vacuo. The base gave an:

$[\alpha]_D^{20} = +86.13$ (C=1, CHCl3)

The NMR spectrum was identical to that obtained for the racemate.

Example 12

4-(piperidin-1-yl)methyl-5-(4-trifluoromethylphenyl)acetyl-4,5,6,7-tetrahydrothieno[3,2-c]pyridine 4.5 g (19.07 mmoles) of 4-(piperidin-1-yl)methyl-4,5,6,7-tetrahydrothieno[3,2-c]pyridine pyridine were dissolved in 100 ml of dry chloroform.

5.8 g (42.03 mmoles) of anhydrous potassium carbonate were added and the slurry cooled at −5° C.

4.7 g (21.12 mmoles) of 4-trifluoromethylphenylacetyl chloride, dissolved in 25 ml of dry chloroform, were added dropwise.

The reaction mixture was kept at +5° C. 1 hour and then allowed to reach room temperature.

50 ml of water were added, the organic layer was separated, washed twice with water, dried over Na2SO4 and evaporated in vacuo to dryness.

The residue was chromatographed on silica gel, eluting with hexane, containing increasing amounts of AcOEt (10–50%), to afford 5.5 g of the free base, which was crystallized from 50 ml of hexane.

$C_{22}H_{25}F_3N_2OS$
M.P. = 88°–89° C.
M.W. = 422.502.

Elemental analysis: Calcd. C, 62.54; H, 5.96; N, 6.63; Found C, 62.41; H, 5.97; N, 6.60. I.R. (KBr): 1650, 1640 (s); 1415 (m); 1325 (s) cm$^{-1}$. N.M.R. (CDCl3): δ6.70–7.70 (m, 6H); 5.65–5.85 (m, 0.5H); 80 Mhz 4.80–5.10 (m, 1H); 3.70–4.30 (m, 2.5H); (50:50 tautomeric 2.00–3.65 (m, 9H); 1.20–1.80 (m, 6H). amides mixture)

Example 13

(−)-4-(piperidin-1-yl)methyl-5-(4-trifluoromethylphenyl)acetyl-4,5,6,7-tetrahydrothieno[3,2-c]pyridine L(+) tartrate monohydrate 3.7 g (8.76 mmoles) of the compound of Ex. No. 12 were dissolved in 60 ml of abs. ethanol. 1.38 g (9.20 mmoles) of L (+) tartaric acid, dissolved in 50 ml of ethanol, were added to the hot solution of the free base.

After a gentle warming the solution was filtered and evaporated in vacuo to dryness.

The residue was dissolved in 100 ml of dry ethyl acetate and left ten days at room temperature.

The distereoisomeric salt was filtered and crystallized several times from ethyl acetate up to a constant rotatory power, to yield 1.1 g of the title compound.
$C_{22}H_{25}F_3N_2OS \cdot C_4H_6O_6 \cdot H_2O$
M.P. = 138°–142° C.
M.W. = 590.606.
$[\alpha]_D^{20} = -44.29$ (C=1, MeOH).

Elemental analysis: Calcd. C, 52.87; H, 5.63; N, 4.74; Found C, 52.71; H, 5.63; N, 4.66.

A sample of tartrate salt was transformed into the free base by dissolving in acq. NH3 solution, extracting with ethyl ether and evaporating the solvent in vacuo. The base gave an:

$[\alpha]_D^{20} = -82.05$ (C=1, CHCl3)

The NMR spectrum was identical to that obtained for the racemate.

Example 14

(+)-4-(piperidin-1-yl)methyl-5-(4-trifluoromethylphenyl)acetyl-4,5,6,7-tetrahydrothieno[3,2-c]pyridine D(−) tartrate monohydrate The mother liquors of the first crystallization of example 13 were evaporated in vacuo to dryness.

The residue was treated with NH4O4 solution and extracted with ethyl ether to afford 2.1 g (4.97 mmoles) of the enriched free base, which was dissolved in 70 ml of hot ethyl acetate. 780 mg (5.20 mmoles) of D (−) tartaric acid were added and the solution left several days at room temperature. The precipitated diastereoisomeric salt was filtered and recrystallized several times from ethyl acetate up to a constant rotatory power, to yield 1.1 g of the title compound.
$C_{22}H_{25}F_3N_2OS \cdot C_4H_6O_6 \cdot H_2O$
M.P. = 140°–142° C.
M.W. = 590.606.
$[\alpha]_D^{20} = +44.31$ (C=1, MeOH).

A sample of tartrate salt was transformed into the free base by dissolving in acq. NH3 solution, extracting with ethyl ether and evaporating the solvent in vacuo. The base gave an:

$[\alpha]_D^{20} = +82.33$ (C=1, CHCl3)

The NMR spectrum was identical to that obtained for the racemate.

Description 5

1-chloromethyl-3,4-dihydro-5H-pyrido[4,3-b]indole dichlorophosphite 2.3 g (9.72 mmoles) of N-chloroacetyl-2-(2-indolyl)ethylamine were dissolved in 25 ml of phosphorus oxychloride.

3.9 g (18.70 mmoles) of phosphorus pentachloride were added portionwise under mechanical stirring and nitrogen atmosphere.

Spontaneously the temperature reached 40° C. and slowly decreased.

After three hours 70 ml of anhydrous diethyl ether were added and the precipitate was filtered off, washed with diethyl ether and dried, to yield 2.2 g of the title compound, which was directly used in the subsequent reaction without further purification.

N.M.R. (CF3COOD): δ7.35–7.75 (m, 4H); 5.15 (s, 2H); 4.20 80 Mhz (t broad, 2H); 3.45 (t broad, 2H).

Description 6

1-(pyrrolidin-1-yl)methyl-1,2,3,4-tetrahydro-5H-pyrido[4,3-b]indole 900 mg (2.55 mmoles) of 1-chloromethyl-3,4-dihydro-5H-pyrido[4,3-b]indole dichlorophosphite were added portionwise under nitrogen atmosphere to a solution of 1 ml (12.08 mmoles) of pyrrolidine in 30 ml of methanol, kept at −10° C. The reaction mixture was allowed to reach room temperature and heated 2 hours at 50° C.

The insaturated intermediate was reduced by treating with 300 mg (7.89 mmoles) of NaBH4 under nitrogen atmosphere at 0° C., three hours.

1 ml of 40% NaOH solution was added and the precipitate inorganic salts filtered off.

The filtrate was evaporated in vacuo to dryness; the residue treated with conc. NaOH solution and exhaustively extracted with CH2Cl2.

The organic solution was dried over Na2SO4 and concentrated in vacuo to afford 600 mg of the crude product which was chromatographed on silica gel, eluting with CH2Cl2, containing 2–8% of MeOH, to yield 300 mg of the title compound.

N.M.R. (CDCl3): 8.40 (s broad, 1H); 7.35–7.58 (m, 1H); 80 Mhz 6.95–7.32 (m, 3H); 4.28–4.47 (m, 1H); 2.50–3.40 (m, 11H); 1.70–1.92 (m, 4H).

Example 15

1-(pyrrolidin-1-yl)methyl-2-(3,4-dichlorophenyl)acetyl-1,2,3,4-tetrahydro-5H-pyrido[4,3-b]indole hydrochloride hemihydrate Prepared as Ex. No. 12, from 300 mg (1.17 mmoles) of 1-(pyrrolidin-1-yl)methyl-1,2,3,4-tetrahydro-5H-pyrido[4,3-b]indole, indole, 325 mg (2.35 mmoles) of anhydrous potassium carbonate and 320 mg (1.43 mmoles) of 3,4-dichlorophenylacetylchloride in 25 ml of dry chloroform.

The silica gel chromatographic column was eluted with CH2Cl2, containing increasing amounts of MeOH (0.5–3%), to afford 280 mg of the free base, which was dissolved in 20 ml of acetone and the solution brought to acidic pH with HCl/diethyl ether. The precipitate was filtered, washed and dried, to yield 110 mg of the title compound.

$C_{24}H_{25}Cl_2N_3O \cdot HCl \cdot \frac{1}{2}H_2O$
M.P. = 180°–184° C.
M.W. = 487.851.

Elemental analysis: Calcd. C, 59.08; H, 5.58; N, 8.61; Found C, 59.14; H, 5.55; N, 8.38. I.R. (KBr): 1640 (s) cm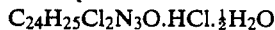.

Description 6a 4-(piperidin-1-yl)methyl-1,2,3,4-tetrahydro-5H-pyrido[4,3-b]indole Prepared as Description No. 6, from 4.6 g (13.01 mmoles) of 1-chloromethyl-1,2,3,4-tetrahydro-5H-pyrido[4,3-b]indole dichlorophosphite and 6.5 ml (65.72 mmoles) of piperidine in 140 ml of MeOH.

The insaturated intermediate was reduced by treating with 1.0 g (126.31 mmoles) of NaBH4 and the working up of the reaction mixture was the same as in Description 6.

The silica gel chromatographic column was eluted with CH2Cl2, containing increasing amounts of MeOH (2–8%), to yield 1.1 g of the title compound.

Elemental analysis: Calcd. C, 65.79; H, 5.96; N, 9.21; Found C, 65.79; H, 6.02; N, 9.07. I.R. (KBr): 3250 (m); 1620 (s); 1470, 1455 (m) cm<sup>−1</sup>. N.M.R. (CDCl3): δ8.00 (broad, 1H); 6.90–7.60 (m, 7H); 80 Mhz. 6.00–6.20 (m, 0.35H); 4.80–5.35 (m, 1.30H) (65:35 tautomeric 3.40–4.45 (m, 2.35H); 2.00–3.30 (m, 9H) amides mixture) 1.30–1.90 (m, 6H).

Example 16

1-(piperidin-1-yl)methyl-2-(3,4-dichlorophenyl)acetyl-1,2,3,4-tetrahydro-5H-pyrido[4,3-b]indole Prepared as Ex. No. 12, from 1.1 g (4.08 mmoles) of crude 1-(piperidin-1-yl)methyl-1,2,3,4-tetrahydro-5H-pyrido[4,3-b]indole, 1.12 g (8.10 mmoles) of anhydrous potassium carbonate and 1.1 g (4.92 mmoles) of 3,4-dichlorophenylacetylchloride in 40 ml of dry chloroform.

The silica gel chromatographic column was eluted with CH2Cl2, containing increasing amounts of MeOH (0.5–1.5%) to afford 380 mg of the free base which was crystallized from a 1:5 mixture of ethyl acetate/isopropyl ether to yield 280 mg of the title compound.

$C_{25}H_{27}Cl_2N_3O$ 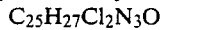
M.P. = 175°–178° C.
M.W. = 456.404.

Description 7

4-(1-chloro)ethyl-6,7-dihydrothieno[3,2-c]pyridine dichlorophosphite 5 g (22.99 mmoles) of N-(2-chloropropionyl)-2-(2-thienyl) ethylamine were dissolved in 21 ml of phosphorus oxychloride.

10 g (47.96 mmoles) of phosphorus pentachloride were added portionwise under mechanical stirring and nitrogen atmosphere.

Spontaneously the temperature reached ·40° C. and slowly decreased. After three hours 40 ml of anhydrous diethyl ether were added and the precipitate was filtered off, washed with diethyl ether and dried, to yield 6.9 g of the title compound, which was directly used in the subsequent reaction without further purification.

N.M.R. (CDCl3): δ7.5 (AB system, J=6 Hz, 2H); 5.8 (9, 1H); 80 Mhz 4.1 (t, 2H); 3.3 (t, 2H); 2.0 (d, 3H).

Description 8

4-[1-(1-dimethylamino)ethyl]-4,5,6,7-tetrahydrothieno[3,2-c]pyridine (mixture of distereoisomeric diamines)

6.9 g (20.62 mmoles) of 4-(1-chloro)ethyl-6,7-dihydrothieno[3,2-c]pyridine dichlorophosphite were added portionwise under nitrogen atmosphere to 60 ml of a 33% dimethylamineethanolic solution kept at −10° C.

The reaction mixture was transferred into a Parr bomb apparatus and heated three days at 90° C.

The insaturated intermediate was reduced by treating with 2.0 g (52.60 mmoles) of NaBH4 under nitrogen atmosphere at room temperature and left overnight. 5 ml of 40% NaOH solution were added and the precipitated inorganic salts filtered off. The filtrate was evaporated in vacuo to dryness, the residue treated with conc. NaOH solution and exaustively extracted with diethyl ether.

The organic solution was dried over Na2SO4 and the solvent evaporated in vacuo to dryness, to afford 4.8 g of the mixture of the diastereoisomeric diamines.

The crude mixture was chromatographed on silica gel, eluting with CH2Cl2 containing increasing amounts of MeOH (0.5–5%), to yield 2.5 g of the pure distereoisomeric diamines (1:3 ratio, detected by G.C.).

The mixture was used without further purification in the following step.

Example 17

4-[1-(1-dimethylamino)ethyl]-5-(3,4-dichlorophenyl)acetyl-4,5,6,7-tetrahydrothieno[3,2-c]pyridine hydrochloride

Diastereoisomer A

Prepared as Example No. 12, from 2.5 g (10.59 mmoles) of the diastereoisomeric mixture of the Description No. 6, 3.0 g (21.74 mmoles) of anhydrous potassium carbonate and 2.83 g (12.66 mmoles) of 3,4-dichlorophenylacetyl chloride in 40 ml of dry chloroform.

The silica gel chromatographic column was eluted with hexane, containing increasing amounts of ethyl acetate (5–30%), to afford 1.05 g of the least polar product, which was dissolved in 30 ml of ethyl acetate and the solution brought to acidic pH with HCl/diethyl ether.

The precipitate was filtered, washed and dried, to yield 830 mg of the title compound, which was recrystallized from acetone.

$C_{19}H_{22}Cl_2N_2OS.HCl$ 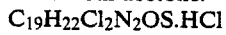

M.P. = 147°–149° C. M.W. = 433.827.

Elemental analysis: Calcd. C, 52.60; H, 5.34; N, 6.46; Found C, 51.94; H, 5.36; N, 6.27. I.R. (KBr): 1655 (s); 1640 (s); 1470 (s); 1405 (s) cm$^{-1}$ N.M.R. (CDCl$_3$): δ11.60 (s broad, 1H); 7.05–7.45 (m, 4H); 80 Mhz 6.88 (d, 1H); 6.05 (d broad, 1H); 4.00–4.45 (m, 1H); 3.95 (AB system, J=16 Hz, 2H); 3.45–3.95 (m, 2H); 2.95 (s, 6H); 2.55–3.15 (m, 2H); 1.40 (d, J=6.5 Hz, 3H).

Example 18

4-[1-(dimethylamino)ethyl]-5-(3,4-dichlorophenyl)acetyl-4,5,6,7-tetrahydrothieno[3,2-c]pyridine hydrochloride

Diastereoisomer B

Continuing the elution of the chromatographic column described in the Example No. 17 with ethyl acetate, containing increasing amounts of MeOH (0.5–2%), 2.7 g of a second product were obtained and dissolved in 70 ml of ethyl acetate.

The solution was brought to acidic pH with HCl/diethyl ether.

The precipitate was filtered, washed and dried, to yield 2.6 g of the title compound.

$C_{19}H_{22}Cl_2N_2OS.HCl$

M.P. = 255°–257° C. M.W. = 433.827

Elemental analysis: Calcd. C, 52.60; H, 5.34; N, 6.46; Found C, 52.75; H, 5.43; N, 6.33. I.R. (KBr): 1655 (s); 1645 (s); 1465 (s); 1435 (s) cm$^{-1}$ N.M.R. (CDCl$_3$): δ11.35 (s broad, 1H); 7.05–7.45 (m, 4H); 80 Mhz 6.80 (d, 1H); 5.82 (d, J=11 Hz, 1H); 4.15–4.35 (m, 1H); 4.05 (AB system, J=16 Hz, 2H); 3.30–3.95 (m, 2H); 2.65–2.95 (m, 8H); 1.45 (d, J=6.5 Hz, 3H).

Example 19

4-(piperidin-1-yl)methyl-5-(5,6,7,8-tetrahydronapht-2-yl) acetyl-4,5,6,7-tetrahydrothieno[3,2-c]pyridine hydrochloride hemihydrate Prepared as Example No. 3, from 550 mg (2.33 mmoles) of 4-(piperidin-1-yl)methyl-4,5,6,7-tetrahydrothieno[3,2-c]pyridine, 530 mg (2.79 mmoles) of 5,6,7,8-tetrahydronapht-2-yl acetic acid and 1.0 g (4.90 mmoles) of dicyclohexylcarbodiimide in 30 ml of dry chloroform. 

The silica gel chromatographic column was eluted with hexane, containing increasing amounts of ethyl acetate (5–40%), to afford 700 mg of the pure free base, which was dissolved in 30 ml of ethyl acetate and the solution brought to acidic pH with HCl/diethyl ether.

The precipitate was filtered, washed and dried, to yield 450 mg of the title compound.

$C_{25}H_{32}N_2OS.HCl.\frac{1}{2}H_2O$

M.P. = 212°–215° C. M.W. = 454.061

Elemental analysis: Calcd. C, 66.12; H, 7.54; N, 6.17; Found C, 65.82; H, 7.37; N, 6.09. I.R. (KBr): 1625 (s); 1435 (m) cm$^{-1}$. N.M.R. (CDCl$_3$): δ11.25 (s broad, 1H); 6.98 (s, 3H); 80 Mhz 6.95 (AB system, J=5.0 Hz, 2H); 6.13 dd, 1H); 4.10–4.45 (m, 2H); 3.95 (d, 2H); 3.20–3.90 (m, 3H); 2.30–3.20 (m, 10H); 1.60–2.10 (m, 9H).

Example 20

4-(piperidin-1-yl)methyl-5-(indan-5-yl)acetyl-4,5,6,7-tetrahydrothieno[3,2-c]pyridine hydrochloride ⅓ hydrate Prepared as Example No. 3, from 1.5 g (6.36 mmoles) of 4-(piperidin-1-yl)methyl-4,5,6,7-tetrahydrothieno[3,2-c]pyridine, 1.3 g (7.39 mmoles) of indan-5-yl acetic acid and 2.4 g (11.76 mmoles) of dicyclohexylcarbodiimide in 50 ml of dry chloroform. 

The silica gel chromatographic column was eluted with CH$_2$Cl$_2$, containing increasing amounts of MeOH (0.3–0.8%), to afford 2.0 g of the pure free base, which was dissolved in 50 ml of ethyl acetate and the solution brought to acidic pH with HCl/diethyl ether.

The precipitate was filtered, washed and dried, to yield 1.34 g of the title compound.

$C_{24}H_{30}N_2OS.HCl.\frac{1}{3}H_2O$

M.P. = 179°–181° C. M.W. = 437.032.

Elemental analysis: Calcd. C, 65.95; H, 7.29; N, 6.40; Found C, 65.94; H, 7.20; N, 6.36. I.R. (KBr): 1640 (s); 1435 (m) cm$^{-1}$. N.M.R. (CDCl$_3$): δ11.25 (s broad, 1H); 6.95–7.20 (m, 4H); 80 Mhz 6.78 (d, 1H); 6.12 (dd, 1H); 4.05–4.45 (m, 2H); 3.98 (d, 2H); 3.20–3.85 (m, 3H); 2.30–3.20 (m, 10H); 1.55–2.30 (m, 7H).

Example 21

4-(pyrrolidin-1-yl)methyl-5-(5,6,7,8-tetrahydronapht-2-yl) acetyl-4,5,6,7-tetrahydrothieno[3,2-c]pyridine hydrochloride Prepared as Example No. 3, from 1.5 g (6.76 mmoles) of 4-(pyrrolidin-1-yl)methyl-4,5,6,7-tetrahydrothieno[3,2-c]pyridine, 1.5 g (7.90 mmoles) of 5,6,7,8-tetrahydronapht-2-yl acetic acid and 2.5 g (12.25 mmoles) of dicyclohexylcarbodiimide in 50 ml of dry chloroform.

The silica gel chromatographic column was eluted with CH$_2$Cl$_2$, containing increasing amounts of MeOH (0.5–2%) to afford 1.4 g of the pure free base, which was dissolved in 40 ml of ethyl acetate and the solution brought to acidic pH with HCl/diethyl ether.

The precipitate was filtered and recrystallized from 20 ml of abs. ethanol to yield 800 mg of the title compound.

$C_{24}H_{30}N_2OS.HCl.$ 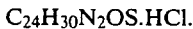

M.P. = 255°–257° C. M.W. = 431.027

Elemental analysis: Calcd. C, 66.87; H, 7.25; N, 6.50; Found C, 66.66; H, 7.25; N, 6.46. I.R. (KBr): 1630 (s); 1420 (m) cm$^{-1}$. N.M.R. (CDCl$_3$): δ11.90 (s broad, 1H); 6.98 (s, 3H); 80 Mhz 6.95 (AB system, J=5.0 Hz, 2H); 6.12 dd, 1H); 3.95–4.45 (m, 2H); 4.00 (s broad, 2H);

3.40–3.82 (m, 3H); 2.35–3.20 (m, 9H); 1.90–2.35 (m, 4H); 1.65–1.85 (m, 4H).

Example 22

4-(pyrrolidin-1-yl)methyl-5-(indan-5-yl)acetyl-4,5,6,7-tetrahydrothieno[3,2-c]pyridine hydrochloride Prepared as Example No. 3, from 1.5 g (6.76 mmoles) of 4-(pyrrolidin-1-yl)methyl-4,5,6,7-tetrahydrothieno[3,2-c]pyridine, 1.4 g (7.95 mmoles) of indan-5-yl acetic acid and 2.4 g (11.76 mmoles) of dicyclohexylcarbodiimide in 50 ml of dry chloroform.

The silica gel chromatographic column was eluted with $CH_2Cl_2$, containing increasing amounts of MeOH (0.2–1.5%), to afrord 1.0 g of the pure free base, which was dissolved in ethyl acetate and the solution brought to acidic pH with HCl/diethyl ether.

The precipitate was filtered and recrystallized from 20 ml of abs. ethanol, to yield 650 mg of the title compound.

$C_{23}H_{28}N_2OS \cdot HCl$

M.P. = 249°–251° C. M.W. = 417.001.

Elemental analysis: Calcd. C, 66.24; H, 7.01; N, 6.72; Found C, 65.89; H, 7.00; N, 6.66. I.R. (KBr): 1635 (s); 1420 (m) cm$^{-1}$. N.M.R. (CDCl$_3$): δ11.80 (s broad, 1H); 6.95–7.20 (m, 4H); 80 Mhz 6.80 (d, 1H); 6.10 (dd, 1H); 4.05–4.45 (m, 2H); 4.05 (d broad, 2H); 3.30–3.85 (m, 3H); 2.45–3.30 (m, 9H); 1.80–2.40 (m, 6H).

Description 9

4,5,6,7-tetrahydroimidazo[4,5-c]pyridine-4-carboxylic acid dihydrochloride 25.00 g (0.135 moles) of histamine dihydrochloride were dissolved in 125 ml of water; 26.92 g (0.40 moles) of 85% potassium hydroxide were then added to the cooled solution. A solution of 12.51 g (0.136 moles) of monohydrate glyoxylic acid and 9.00 g (0.136 moles) of 85% potassium hydroxyde in 125 ml of water was dropped into the first one and the reaction mixture heated at 90° C., 6 hours, cooled, treated with conc. HCl and concentrated in vacuo to dryness.

The residue was extracted three times with hot methanol and the inorganic salts filtered off.

The filtrate was concentrated in vacuo to yield 32.3 g of the title compounds which was used without further purification in the following step.

Description 10

4,5,6,7-tetrahydroimidazo[4,5-c]pyridine-4-carboxylic acid methyl ester dihydrochloride 32.3 g (0.134 moles) of 4,5,6,7-tetrahydroimidazo[4,5-c]pyridine-4-carboxylic acid dihydrochloride in 500 ml of methanol were treated below −5° C. with 16 ml (0.220 moles) of SOCl$_2$.

The reaction mixture was heated 3 hours at 60° C., filtered over celite and the filtrate concentrated in vacuo to dryness, to yield 32.0 g of the title compound, which was used without further purification in the following step.

Description 11

4-(pyrrolidin-1-yl)carbonyl-4,5,6,7-tetrahydroimidazo[4,5-c]pyridine 30.4 g (0.120 moles) of the crude 4,5,6,7-tetrahydroimidazo[4,5-c]pyridine-4-carboxylic acid methyl ester dihydrochloride were cooled at −15° C. and 100 ml (1.20 moles) of pyrrolidine added dropwise.

After 24 hours the reaction mixture was concentrated in vacuo to dryness to afford a residue which was treated with conc. NaOH solution and exhaustively extracted with $CH_2Cl_2$, containing 5% of MeOH.

The organic solution was dried over $Na_2SO_4$ and the solvent evaporated in vacuo to dryness.

The residue was chromatographed on silica gel, eluting with $CH_2Cl_2$, containing increasing amounts of MeOH (1–10%), to yield 4.8 g of the title compound.

$C_{11}H_{16}N_4O$

M.P. = 212–215. M.W. = 220.27.

Elemental analysis: Calcd. C, 59.98, H, 7.32; N, 25.44; Found C, 59.34; H, 7.32; N, 24.90. I.R. (KBr): 3305 (m); 1620 (s); 1595 (m) cm$^{-1}$. N.M.R. (CDCl$_3$): δ7.40 (s, 1H); 4.85 (s broad, 1H); 80 Mhz 2.50–4.30 (m, 9H); 1.80–2.10 (m, 4H).

Description 12

4-(pyrrolidin-1-yl)methyl-4,5,6,7-tetrahydroimidazo[4,5-c]pyridine 3.63 g (16.48 mmoles) of 4-(pyrrolidin-1-yl)carbonyl-4,5,6,7-tetrahydroimidazo[4,5-c]pyridine were added portionwise, at room temperature, under nitrogen atmosphere, to a slurry of 1.00 g (26.32 mmoles) of lithium aluminium hydride in 180 ml of dry dioxane.

The reaction mixture was then heated 30 hours at 90° C. After an alkaline work-up, 2.9 g of the crude product were obtained and chromatographed on silica gel, eluting with $CH_2Cl_2$, containing increasing amounts of MeOH (2–12%) and 32% NH$_4$OH solution (0.5–2%) to yield 900 mg of the title compound.

N.M.R. (CDCl$_3$+D$_2$O): δ7.45 (s, 1H); 4.00 (m, 1H); 80 Mhz 2.50–3.40 (m, 10H); 1.65–1.90 (m, 4H).

Example 23

4-(pyrrolidin-1-yl)methyl-5-(3,4-dichlorophenyl)acetyl-4,5,6,7-tetrahydroimidazo[4,5-c]pyridine Prepared as Example No. 12, from 900 mg (4.37 mmoles) of 4-(pyrrolidin-1-yl)methyl-4,5,6,7-tetrahydroimidazo[4,5-c]pyridine, 950 mg (6.88 mmoles) of anhydrous potassium carbonate and 1.30 g (5.80 mmoles) of 3,4-dichlorophenylacetyl chloride in 35 ml of dry chloroform.

The silica gel chromatographic column was eluted with $CH_2Cl_2$, containing increasing amounts of MeOH (2–8%) and 32% Na$_4$OH solution (0.2–0.8%), to afford 1.0 g of the free base which was recrystallized from ethyl acetate/hexane to yield 900 mg of the title compound.

$C_{19}H_{22}Cl_2N_4O$

M.P. = 84° C. M.W. = 393.312.

I.R. (KBr): 1640 (s); 1450 (m) cm$^{-1}$.

N.M.R. (CDCl$_3$): 7.45 (s, 1H); 6.95–7.38 (m, 3H); 5.60 80 Mhz (t broad, 0.6H); 4.80–5.10 (m, 0.6H); (60:40 thautomeric 2.40–4.10 (m, 11.8H); 1.65–1.95 (m, 4H). amides mixture)

Example 24

(+)-4-(pyrrolidin-1-yl)methyl-5-(5,6,7,8-tetrahydronapht-2-yl)acetyl-4,5,6,7-tetrahydrothieno[3,2-c]pyridine hydrochloride 5.57 g (14.12 mmoles) of the compound of Ex. No. 21 were dissolved in 100 ml of abs. ethanol. 2.21 g (14.72 mmoles) of L(+) tartaric acid, dissolved in 70 ml of ethanol, were added to the hot solution of the free base.

After a gentle warming the solution was filtered and the less soluble diastereoisomeric salt crystallized on standing.

The salt was recrystallized from 95% ethanol, up to a constant rotatory power, to give 1.5 g of L(+) tartrate.

M.P. = 193°–194° C.

$[\alpha]_D^{20} = +80.33$ (C=1, MeOH).

The tartrate salt was transformed into the free base by dissolving in acq. NH$_3$ solution, extracting with diethyl ether and evaporating the solvent in vacuo.

The obtained free base was dissolved in 50 ml of ethyl acetate, containing 20% acetone, and the solution was brought to acidic pH with HCl/diethyl ether.

The precipitate was filtered, washed and dried to yield 650 mg of the title compound.

$C_{24}H_{30}N_2OS \cdot HCl$

M.P. = 176°–177° C. M.W. = 431.027.

$[\alpha]_D^{20} = +91.94$ (C=1, MeOH).

Elemental analysis: Calcd. C, 66.87; H, 7.25; N, 6.50; Cl, 8.23; S, 7.44; Found C, 66.68; H, 7.27; N, 6.44; Cl, 8.28; S, 7.46.

The I.R. and N.M.R. spectra were identical to those obtained for the racemate.

Example 25

(−)-4-(pyrrolidin-1-yl)methyl-5-(5,6,7,8-tetrahydronapht-2-yl)acetyl-4,5,6,7-tetrahydrothieno [3,2-c] pyridine hydrochloride The mother liquors of the first crystallization of Ex. No. 24 were evaporated in vacuo to dryness. The residue was treated with acq. NH$_3$ solution and extracted with diethyl ether to afford 3.56 g (9.02 mmoles) of the enriched free base, which was dissolved in 80 ml of abs. ethanol. 1.41 g (9.39 mmoles) of D(−) tartaric acid, dissolved in abs. ethanol, were added to the warm solution and the diastereoisomeric salt crystallized on standing.

The salt was recrystallized from 95% ethanol, up to a constant rotatory power, to give 2.48 g of D(−) tartrate.

M.P. = 193°–194° C.

$[\alpha]_D^{20} = -81.20$ (C=1, MeOH).

The tartrate salt was transformed into the free base by dissolving in acq. NH$_3$ solution, extracting with diethyl ether and evaporating the solvent in vacuo.

The obtained free base was dissolved in 80 ml of ethyl acetate, containing 20% acetone, and the solution was brought to acidic pH with HCl/diethyl ether.

The precipitate was filtered, washed and dried to yield 1.4 g of the title compound.

$C_{24}H_{30}N_2OS \cdot HCl$.

M.P. = 175°–176° C. M.W. = 431.027.

$[\alpha]_D^{20} = -91.22$ (C=1, MeOH).

Elemental analysis: Calcd. C, 66.87; H, 7.25; N, 6.50; Cl, 8.23; S, 7.44; Found C, 66.78; H, 7.26; N, 6.43; Cl, 8.26; S, 7.43.

The I.R. and N.M.R. spectra were identical to those obtained for the racemate.

TABLE I

Examples 1 to 25 are summarised in Table 1

| Example No. | Het. | R | R$_1$ | R$_2$ | R$_3$ | R$_4$ | R$_5$ | Molecular Formula | Melting Point (°C.) | $[\alpha]_D^{20}$ C = 1, MeOH |
|---|---|---|---|---|---|---|---|---|---|---|
| 1 | pyridine (N), R$_5$ | 2,4-diCl-C$_6$H$_3$-CH$_2$- | pyrrolidine | | H | CH$_3$ | H | C$_{20}$H$_{23}$Cl$_2$N$_3$O.2C$_4$H$_4$O$_4$ | 130-132 | |
| 2 | thiophene (S), R$_5$ | 2,4-diCl-C$_6$H$_3$-CH$_2$- | pyrrolidine | | H | CH$_3$ | H | C$_{19}$H$_{22}$Cl$_2$N$_2$OS.HCl | 214-215 | |
| 3 | thiophene (S), R$_5$ | 2,4-diCl-C$_6$H$_3$-CH$_2$- | pyrrolidine | | H | —CH$_2$—CH$_2$— | | C$_{20}$H$_{22}$Cl$_2$N$_2$OS.HCl.H$_2$O | 153-155 | |
| 4 | thiophene (S), R$_5$ | 4-CF$_3$-C$_6$H$_4$-CH$_2$- | pyrrolidine | | H | —CH$_2$—CH$_2$— | | C$_{21}$H$_{23}$F$_3$N$_2$OS.HCl | 221-222 | |
| 5 | thiophene (S), R$_5$ | 2,4-diCl-C$_6$H$_3$-CH$_2$- | piperidine | | H | —CH$_2$—CH$_2$— | | C$_{21}$H$_{24}$Cl$_2$N$_2$OS.HCl | 213-214 | |

TABLE I-continued

Examples 1 to 25 are summarised in Table 1

$$\underset{Het}{\overset{R_5}{\bigcirc}}\overset{R_4}{\underset{CHR_3}{\overset{|}{C}}}\overset{COR}{\underset{N}{\overset{|}{N}}}\overset{COR}{\underset{R_2}{\overset{|}{N}}} \quad (I)$$

| Example No. | Het. | R | $R_1$ | $R_2$ | $R_3$ | $R_4$ | $R_5$ | Molecular Formula | Melting Point (°C.) | $[\alpha]_D^{20}$ C = 1, MeOH |
|---|---|---|---|---|---|---|---|---|---|---|
| 6 | S (thiophene with $R_5$) | 2,4-dichlorobenzyl (–CH$_2$–C$_6$H$_3$Cl$_2$) | CH$_3$ | CH$_3$ | H | –CH$_2$–CH$_2$– | | C$_{18}$H$_{20}$Cl$_2$N$_2$OS.HCl | 255–256 | |
| 7 | S (thiophene with $R_5$) | 4-CF$_3$-benzyl (–CH$_2$–C$_6$H$_4$CF$_3$) | CH$_3$ | CH$_3$ | H | –CH$_2$–CH$_2$– | | C$_{19}$H$_{21}$F$_3$N$_2$OS.1/5HCl.½H$_2$O | 257–258 | |
| 8 | S (thiophene with $R_5$) | 2,4-dichlorobenzyl (–CH$_2$–C$_6$H$_3$Cl$_2$) | \multicolumn{2}{c}{pyrrolidine} | H | –CH$_2$–CH$_2$– | | C$_{20}$H$_{22}$Cl$_2$N$_2$OS.C$_4$H$_6$O$_6$.½H$_2$O | 181–183 | +60.34 |
| 9 | S (thiophene with $R_5$) | 2,4-dichlorobenzyl (–CH$_2$–C$_6$H$_3$Cl$_2$) | \multicolumn{2}{c}{pyrrolidine} | H | –CH$_2$–CH$_2$– | | C$_{20}$H$_{22}$Cl$_2$N$_2$OS.C$_4$H$_6$O$_6$.½H$_2$O | 182–183 | −60.39 |

TABLE I-continued

Examples 1 to 25 are summarised in Table 1

| Example No. | Het-R_5 | R | R_1 | R_2 | R_3 | R_4 | R_5 | Molecular Formula | Melting Point (°C.) | $[\alpha]_D^{20}$ C = 1, MeOH |
|---|---|---|---|---|---|---|---|---|---|---|
| 10 | thiophene-R_5 | 3,4-di-Cl-C_6H_3-CH_2- | cyclohexyl | | H | —CH_2—CH_2— | | $C_{21}H_{24}Cl_2N_2OS \cdot C_4H_6O_6 \cdot \tfrac{1}{2}H_2O$ | 170–171 | −49.95 |
| 11 | thiophene-R_5 | 3,4-di-Cl-C_6H_3-CH_2- | cyclohexyl | | H | —CH_2—CH_2— | | $C_{21}H_{24}Cl_2N_2OS \cdot C_4H_6O_6 \cdot \tfrac{1}{2}H_2O$ | 171–172 | +49.46 |
| 12 | thiophene-R_5 | 4-CF_3-C_6H_4-CH_2- | cyclohexyl | | H | —CH_2—CH_2— | | $C_{22}H_{25}F_3N_2OS$ | 88–89 | — |
| 13 | thiophene-R_5 | 4-CF_3-C_6H_4-CH_2- | cyclohexyl | | H | —CH_2—CH_2— | | $C_{22}H_{25}F_3N_2OS \cdot C_4H_6O_6 \cdot H_2O$ | 138–142 | −44.29 |
| 14 | thiophene-R_5 | 4-CF_3-C_6H_4-CH_2- | cyclohexyl | | H | —CH_2—CH_2— | | $C_{22}H_{25}F_3N_2OS \cdot C_4H_6O_6 \cdot H_2O$ | 140–142 | +44.31 |

TABLE I-continued

Examples 1 to 25 are summarised in Table 1

$$\underset{\text{Het}}{\overset{R_5}{\bigcirc}}-\underset{\underset{R_1}{\overset{|}{N}}\underset{R_2}{}}{\overset{CHR_3}{\mid}}-\underset{\underset{COR}{\overset{|}{N}}}{\overset{R_4}{\mid}} \quad (I)$$

| Example No. | Het. with $R_5$ | R | $R_1$ | $R_2$ | $R_3$ | $R_4$ | $R_5$ | Molecular Formula | Melting Point (°C.) | $[\alpha]_D^{20}$ C = 1, MeOH |
|---|---|---|---|---|---|---|---|---|---|---|
| 15 | indole (NH) with $R_5$ | 2,3-diCl-benzyl (—CH$_2$—) | pyrrolidine | | H | —CH$_2$—CH$_2$— | | $C_{24}H_{25}Cl_2N_3O.HCl.\tfrac{1}{2}H_2O$ | 180–184 | — |
| 16 | indole (NH) with $R_5$ | 2,3-diCl-benzyl (—CH$_2$—) | piperidine | | H | —CH$_2$—CH$_2$— | | $C_{25}H_{27}Cl_2N_3O$ | 175–178 | — |
| 17 | thiophene (S) with $R_5$ | 2,3-diCl-benzyl (—CH$_2$—) | CH$_3$ | CH$_3$ | CH$_3$ | —CH$_2$—CH$_2$— | | $C_{19}H_{22}Cl_2N_2OS.HCl$ | 147–149 | — |
| 18 | thiophene (S) with $R_5$ | 2,3-diCl-benzyl (—CH$_2$—) | CH$_3$ | CH$_3$ | CH$_3$ | —CH$_2$—CH$_2$— | | $C_{19}H_{22}Cl_2N_2OS.HCl$ | 255–257 | — |

TABLE I-continued
Examples 1 to 25 are summarised in Table 1
$$\begin{array}{c} R_5 \\ Het \end{array} \begin{array}{c} R_4 \\ N \\ CHR_3 \\ R_1 \\ N \\ R_2 \end{array} \begin{array}{c} COR \end{array} \quad (I)$$
| Example No. | Het. | R | R₁ | R₂ | R₃ | R₄ | R₅ | Molecular Formula | Melting Point (°C.) | $[\alpha]_D^{20}$ C = 1, MeOH |
|---|---|---|---|---|---|---|---|---|---|---|
| 19 | 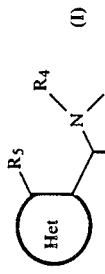 |  | 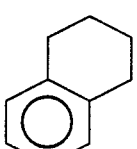 | | H | —CH₂—CH₂— | | $C_{25}H_{32}N_2OS.HCl.\tfrac{1}{2}H_2O$ | 212–215 | — |
| 20 | 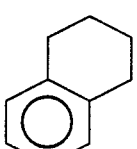 |  |  | | H | —CH₂—CH₂— | | $C_{24}H_{30}N_2OS.HCl.\tfrac{1}{2}H_2O$ | 179–181 | — |
| 21 | 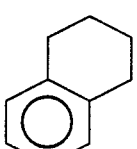 |  | 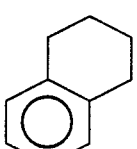 | | H | —CH₂—CH₂— | | $C_{24}H_{30}N_2OS.HCl$ | 255–257 | — |
| 22 | 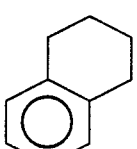 |  |  | | H | —CH₂—CH₂— | | $C_{23}H_{28}N_2OS.HCl$ | 249–251 | — |

TABLE I-continued
Examples 1 to 25 are summarised in Table 1
| Example No. | Het. | R | $R_1$ | $R_2$ | $R_3$ | $R_4$ | $R_5$ | Molecular Formula | Melting Point (°C.) | $[\alpha]_D^{20}$ C = 1, MeOH |
|---|---|---|---|---|---|---|---|---|---|---|
| 23 | 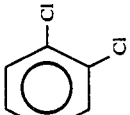 |  |  | | H | —CH$_2$—CH$_2$— | | $C_{19}H_{22}Cl_2N_4O$ | 84 | — |
| 24 |  | 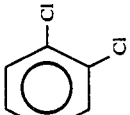 |  | | H | —CH$_2$—CH$_2$— | | $C_{24}H_{30}N_2OS \cdot HCl$ | 176–177 | +91.94 |
| 25 |  |  |  | | H | —CH$_2$—CH$_2$— | | $C_{24}H_{30}N_2OS \cdot HCl$ | 175–176 | −91.22 |

The pharmacological activity of the compounds of this invention is illustrated by various in vitro and in vivo models, using the following test procedures, in which the mouse tail flick test demonstrate analgesic activity.

The results of the tests are given in Table (II).

Mouse Tail-flick test (Modified from the procedure published by D'Amour et al., J. Pharm. Exptl. Ther.72, 74/1941)

Male Charles River mice, average weight 26 g, are used. Selection is carried out before beginning of experiments: only mice whose reaction time is less than 8 sec are used. They are randomly distributed into groups of 10 and dosed with compounds under test, with positive and negative controls being included.

Compounds under test are administered subcutaneously in isotonic saline in a volume of 20 ml. $Kg^{-1}$. 30 min later mice are placed again under heat source (Socrel apparatus) and reaction time is recorded.

The analgesic activity of the test compound is expressed as the percent number of mice doubling the initial time within a group.

% analgesia = No. of mice doubling the reaction time × 100 Total no. of mice per group.

P-phenylquinone-induced abdominal writhing test in mice

The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25–36 g body weight, are used. Animals are allowed food and water ad libitum and are randomized into groups of 10 prior to experimentation. Test compounds are dissolved in either distilled water or distilled water plus 0.1M AMS, and administered by the subcutaneous route in a final volume of 10 ml/Kg. Control animals receive 10 ml/Kg of the appropriate vehicle alone. Following a pretreatment period of 20 min., mice are injected intraperitoneally with p-phenylquinone, 2 mg/Kg at 37° C. in a final volume of 10 mg/Kg. Next, the mice are placed, in a groups of 3, in a compartmented perspex box maintained at room temperature and are observed for a period of 8 min. During this period the number of abdominal writhing responses per animal are recorded where writhing consists of an intermittent contraction of the abdomen associated with hind leg extension.

The degree of antinociceptive protection afforded by the test compound is determined as the mean number of writhing responses observed in the treated group (T) expressed as a percentage of the mean number of writhing responses in the control group (C) according to the following formula:

$[1-(T/C)] \times 100\% = \%$ graded protection.

RECEPTOR AFFINITY STUDY

Tissue preparation

Radio receptor binding to $\mu$ and K sites is performed on fresh guinea pig brain homogenate prepared according to Kosterlitz. (1981).

Whole brain without cerebellum is homogenized in 50 mM, Tris-buffer (pH 7.4 at 0° C.) and centrifuged at 49,000× g × 10 min.

The pellet is then resuspended in the same buffer, incubated at 37° C. for 45 min. and centrifuged again.

1.9 ml of the final homogenate (1:100 in Tris-pH 7.4, 0° C.) is used for the binding assay.

Binding to $\mu$ sites (Magnan J., 1982)

$^3H$ [D-Ala$^2$, MePhe$^4$, Gly-ol$^5$] Enkephalin ($^3$H-DAGO), an enkephalin analogue that binds selectively to $\mu$ receptor, is added to the biological substrate and incubated at 25° C. for 40 min., filtered through Whatman GF-C and washed with ice-cold Tris-buffer.

The filters are then dryed, solubilized in Filtercount and the radioactivity monitored. Non specific binding is determined in the presence of $10^{-6}$M Naloxone.

Binding to K sites (Magnan J., 1982)

The binding of tritiated Ethylketocyclazocine to brain homogenate is measured the in presence of 100 nanomolar D-Ala-D-LeuEnkephalin (DADLE) and 100 nanomolar DAGO, added to saturate the $\delta$ and $\mu$ opioid receptors respectively.

Final homogenate with solutions of the cold ligand and of the labelled ligand is incubated for 40 min. at 25° C., filtered through Whatman GF/C glass filter discs and washed.

The radioactivity bound to the filters is counted by liquid scintillation spectrophotometry.

MR 2266.500 nM is utilized to determine the saturable binding.

For the calculation of the kinetic parameters of the binding of labelled and unlabelled ligands, the equilibrium dissociation constant ($K_D$), the inhibition constant (Ki) and the maximum number of binding sites (B max) are determined from saturation curves and competition experiments (Hill 1910; Scatchard 1949; Cheng and Prusoff 1973; Gillan et al. 1980).

A concentration of radioligand near $K_D$ is used in the binding assays evaluating our compounds.

Published references are listed as follows:

Hill, A. V. (1910): J. Physiol.40, IV–VIII (1910).
Scatchard G. (1949): Ann. N.Y. Acad.Sci., 51, 660–674.
Cheng and Prusoff W. H. (1973): Biochem. Pharmac.22, 3099–3102.
Gillan M. G. C., Kosterlitz H. W.: Br.J. Pharmac. 70, and Paterson S. Y. (1980) 481–490.
Kotsterliz H. W., Paterson S. Y.: Br.J. Pharmac. 73, and Robson L. E. (1981) 939–949.
Magnan J., Paterson S. Y.,: Arch. Pharmacol.319, Tavani A., and Kosterlits 197–205. H. W. (1982)

TABLE II

| | ANALGESIA | | | |
| | WRITHING | TAIL-FLICK | OPIATE RECEPTORS | |
| Ex. | ED50 (a) | ED50 (a) | BINDING ki = nM | |
| No. | (mg/kg s.c.) | (mg/kg s.c.) | KAPPA | MU |
|---|---|---|---|---|
| 2 | | 0.127 | 1.99 | 144 |
| 3 | 0.004 | 0.019 | 1.19 | 85 |
| 4 | 0.004 | 0.018 | 1.78 | 39.2 |
| 5 | 0.022 | 0.090 | 1.29 | 781 |
| 6 | | 0.042 | 1.75 | 607 |
| 7 | | 0.093 | 3.46 | 513 |
| 9 | 0.003 | 0.007 | 1.07 | 47.2 |
| 10 | 0.010 | 0.041 | | 500 |
| 12 | 0.034 | 0.090 | | 793 |
| 13 | 0.010 | 0.054 | | 468 |
| 15 | >10 | >10 | | |
| 16 | >10 | >10 | | |
| 18 | 0.204 | 0.824 | | |
| 19 | 0.092 | 0.220 | | |
| 20 | 0.092 | 0.412 | | |
| 21 | 0.022 | 0.236 | | 56 |

TABLE II-continued

| | ANALGESIA | | OPIATE RECEPTORS BINDING ki = nM | |
|---|---|---|---|---|
| Ex. No. | WRITHING ED50 (a) (mg/kg s.c.) | TAIL-FLICK ED50 (a) (mg/kg s.c.) | KAPPA | MU |
| 22 | 0.014 | 0.146 | | 104 |
| 23 | | >50 | | >1000 |

(a) Calculated for the free base

We claim:

1. A compound, or a solvate or salt thereof, of formula I:

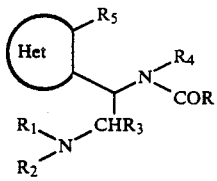

in which:
R.CO— is an acyl group containing a substituted or unsubstituted carbocyclic aromatic or heterocyclic aromatic group;
$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups or together form a $C_{2-8}$ branched or linear polymethylene or $C_{2-6}$ alkenylene group, optionally substituted with a hetero-atom;
$R_3$ is hydrogen, $C_{1-6}$ alkyl, or phenyl or $R_3$ together with $R_1$ form a —(CH$_2$)$_3$— or —(CH$_2$)$_4$— group;
$R_4$ and $R_5$ together form a —(CH$_2$)$_n$— group in which n=1, 2 or 3; and
'Het' is a single ring aromatic heterocyclic group, containing from 5 to 12 ring atoms and comprising up to four hetero-atoms in the ring selected from oxygen, nitrogen and sulphur.

2. A compound according to claim 1, in which each of $R_1$ and $R_2$ is methyl, ethyl, propyl, butyl, pentyl or hexyl.

3. A compound according to claim 1, in which $R_1$ and $R_2$ form a propylene, butylene, pentylene or hexylene group, or a —CH$_2$—CH=CH—CH$_2$—group.

4. A compound according to claim 1 in which 'Het' is a single ring containing one or two sulphur or nitrogen atoms.

5. A compound according to claim 1 in which R has the formula (II)

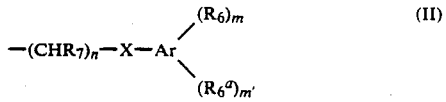

in which
n is 0, 1 or 2,
m is 0, 1 or 2,
m' is 0, 1 or 2, provided m+m'≦2;
X is a direct bond, or O, S or NR$_8$ in which R$_8$ is hydrogen or $C_{1-6}$ alkyl;
Ar is a substituted or unsubstituted carbocyclic aromatic or heterocyclic aromatic group;
each of $R_6$ and $R_6^a$ is $C_{1-6}$ alkyl, $C_{2-6}$ alkenyl, $C_{1-6}$ haloalkyl, $C_{2-6}$ haloalkenyl, $C_{2-6}$ haloalkynyl, aryl, aralkyl, hydroxy, $C_{1-6}$ alkoxy, $C_{1-6}$ haloalkoxy, thiol, $C_{1-6}$ alkylthio, $C_{1-6}$ haloalkylthio, halogen, nitro, cyano, carboxy, $C_{1-6}$ alkoxy-, aryloxy-or aralkoxycarbonyl, carbamoyl, sulfonyl, sulfamoyl, or when m is 2 and m' is O, two R6's form a $C_{3-6}$ polymethylene group,
and $R_7$ is hydrogen or $C_{1-6}$ alkyl.

6. A compound according to claim 5 in which R represents a group selected from

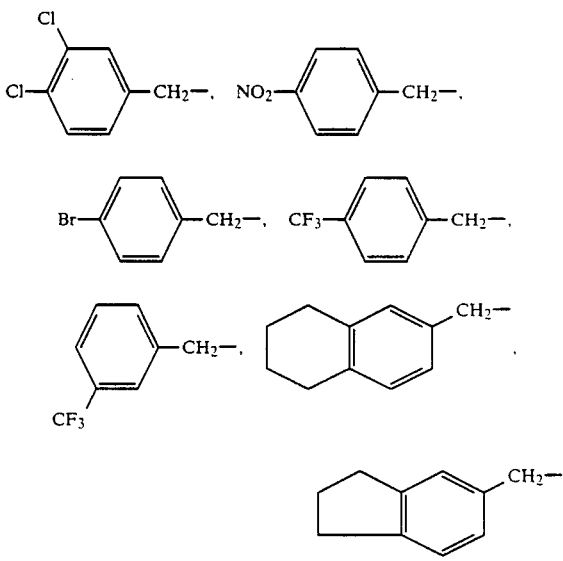

7. A compound selected from the group consisting of:
N-methyl-N-[1-(thien-3-yl)-2-(pyrrolidin-1-yl) ethyl-3,4-dichlorobenzene acetamide;
4-(pyrrolidin-1-yl)methyl-5-(3,4-dichlorophenyl)acetyl-4,5,6,7-tetrahydrothieno [3,2-c] pyridine;
4-(pyrrolidin-1-yl)methyl-5-(4-trifluoromethylphenyl)acetyl-4,5,6,7-tetrahydrothieno [3,2-c] pyridine;
4-(piperidin-1-yl)methyl-5-(3,4-dichlorophenyl)acetyl-4,5,6,7-tetrahydrothieno [3,2-c] pyridine;
4-dimethylaminomethyl-5-(3,4-dichlorophenyl)acetyl-4,5,6,7-tetrahydrothieno [3,2-c] pyridine;
4-dimethylaminomethyl-5-(4-fluoromethylphenyl)acetyl-4,5,6,7-tetrahydrothieno [3,2-c] pyridine;
(+)-4-(pyrrolidin-1-yl)methyl-5-(3,4-dichlorophenyl)acetyl-4,5,6,7-tetrahydrothieno [3,2-c] pyridine;
(−)-4-(pyrrolidin-1-yl)methyl-5-(3,4-dichlorophenyl)acetyl-4,5,6,7-tetrahydrothieno [3,2-c] pyridine;
(−)-4-(piperidin-1-yl)methyl-5-(3,4-dichlorophenyl)acetyl-4,5,6,7-tetrahydrothieno [3,2-c] pyridine;
(+)-4-(piperidin-1-yl)methyl-5-(3,4-dichlorophenyl)acetyl-4,5,6,7-tetrahydrothieno [3,2-c] pyridine;
4-(piperidin-1-yl)methyl-5-(4-trifluoromethylphenyl)acetyl-4,5,6,7-tetrahydrothieno [3,2-c] pyridine;
(−)-4-(piperidin-1-yl)methyl-5-(4-trifluoromethylphenyl)acetyl-4,5,6,7-tetrahydrothieno [3,2-c] pyridine;
(+)-4-(piperidin-1-yl)methyl-5-(4-trifluoromethylphenyl)acetyl-4,5,6,7-tetrahydrothieno [3,2-c] pyridine;
4-[1-(dimethylamino)ethyl]-5-(3,4-dichlorophenyl)acetyl-4,5,6,7-tetrahydrothieno [3,2-c] pyridine;
4-(piperidin-1-yl)methyl-5-(5,6,7,8-tetrahydronaphth-2-yl)acetyl-4,5,6,7-tetrahydrothieno [3,2-c] pyridine;
4-(piperidin-1-yl)methyl-5-(indan-5-yl)acetyl-4,5,6,7-tetrahydrothieno [3,2-c] pyridine;

4-(pyrrolidin-1-yl)methyl-5-(5,6,7,8-tetrahydronaphth-2-yl)acetyl-4,5,6,7-tetrahydrothieno [3,2-c] pyridine;

4-(pyrrolidin-1-yl)methyl-5-(indan-5-yl)acetyl-4,5,6,7-tetrahydrothieno [3,2-c] pyridine;

4-(pyrrolidin-1-yl)methyl-5-(3,4-dichlorophenyl)acetyl-4,5,6,7-tetrahydroimidazo [4,5-c] pyridine;

(+)-4-(pyrrolidin-1-yl)methyl-5-(5,6,7,8-tetrahydronaphth-2-yl)acetyl-4,5,6,7-tetrahydrothieno [3,2-c] pyridine; and (−)-4-(pyrrolidin-1-yl)methyl-5-(5,6,7,8-tetrahydronaphth-2-yl)acetyl-4,5,6,7-tetrahydrothieno [3,2-c] pyridine.

8. A pharmaceutical composition for treating pain in mammals, comprising an effective non-toxic amount of a compound according to claim 1, and a pharmaceutically acceptable carrier.

9. A composition according to claim 8 in unit dosage form.

10. A method of treating pain in mammals which comprises administering an effective non-toxic amount of a compound according to claim 1 to a sufferer.

* * * * *